United States Patent [19]
Smith

[11] 3,960,006
[45] June 1, 1976

[54] NON-DESTRUCTIVE TEST APPARATUS AND METHOD FOR A MATERIAL HAVING A CAVITY THEREIN

[75] Inventor: Robert D. Smith, Elk Grove Village, Ill.

[73] Assignee: Alco Standard Corporation, Valley Forge, Pa.

[22] Filed: Dec. 3, 1973

[21] Appl. No.: 421,131

[52] U.S. Cl.............................. 73/67.8 S; 73/71.5 US
[51] Int. Cl.²......................................... G01N 29/04
[58] Field of Search............ 73/67.8 S, 67.8 R, 67.7, 73/67.9, 71.5 US, 67.5 R

[56] References Cited
UNITED STATES PATENTS

| | | | |
|---|---|---|---|
| 3,021,706 | 2/1962 | Cook et al. | 73/67.8 S |
| 3,272,000 | 9/1966 | Stebbins | 73/67.8 S X |
| 3,455,150 | 7/1969 | Wood | 73/67.8 S X |
| 3,470,868 | 10/1969 | Krause et al. | 73/67.8 S |
| 3,508,436 | 4/1970 | Krautkramer | 73/67.5 R |
| 3,600,613 | 8/1971 | Clarke | 73/67.8 S X |
| 3,732,946 | 5/1973 | McKnight | 73/67.8 R X |
| 3,780,571 | 12/1973 | Wiesener | 73/71.5 US |

*Primary Examiner*—Jerry W. Myracle
*Assistant Examiner*—Stephen A. Kreitman
*Attorney, Agent, or Firm*—Haight, Hofeldt, Davis & Jambor

[57] ABSTRACT

In order to detect flaws in a material having a cavity, such as a turbine rotor with a central bore, a test apparatus utilizing ultrasonic signals or waves in longitudinal, shear and surface modes, or various combinations thereof, is provided. A source of ultrasonic waves is appropriately mounted for both circumferential and axial sweeps of at least a portion of the bore. Appropriate indexing arrangements are provided to accurately determine the axial and circumferential positions of the source, and hence of any detected flaws.

13 Claims, 1 Drawing Figure

U.S. Patent June 1, 1976 3,960,006
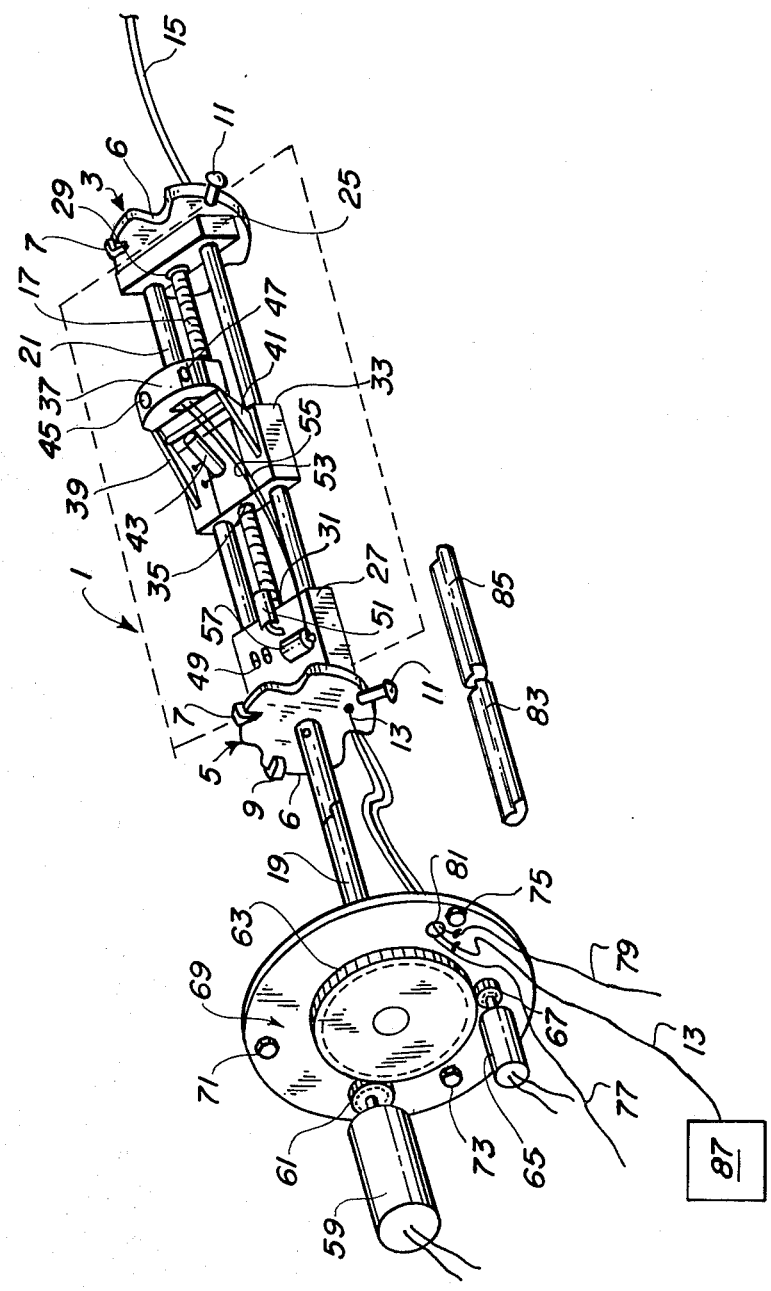

NON-DESTRUCTIVE TEST APPARATUS AND METHOD FOR A MATERIAL HAVING A CAVITY THEREIN

BACKGROUND OF THE INVENTION

1. Field of the Invention

This invention relates generally to a flaw detecting apparatus inserted into a cavity of a material being tested, and, more specifically, this invention relates to the utilization of a test apparatus employing ultrasonic waves which is inserted into the bore of a turbine rotor to detect flaws in the material of the rotor.

2. Description of the Prior Art

As turbine sizes have increased over the years in response to the requirements of greater power output, the necessity of improved strength and operational characteristics has created corresponding design problems. Failure of a very large turbine involves not only the considerable expense of repair or replacement, but also frequently results in unacceptable power shortages. Further, the dangers inherent in the forcible failure of a turbine is increased with turbine size. To decrease the chances of turbine failure or shortened operational life, improved materials and better quality control have been utilized.

One of the problems that exists in connection with applying quality control standards to forged turbine rotors is the necessity of determining the existence of flaws that could weaken the rotors and decrease the useful life thereof. Such flaws include items such as cracks, non-metallic inclusions or voids. Various steps have been taken to detect such flaws in a forged turbine rotor, but none of the prior art methods gives the desired reliability, detailed information regarding the flaw, and reproducibility of the test that are required for improved quality control.

For some time, peripheral scanning of the exterior of a rotor by utilization of pulse-echo techniques has been employed. As these tests can be made quite sensitive, they are useful for evaluating initial forging quality. However, the initially forged rotors are considerably altered during the machining cycle, thus making it impossible to duplicate the initial peripheral tests. This makes comparative testing impossible, and hence restricts the utility of this approach. The only surface of the rotor which remains unchanged and accessible to testing is the bore of the rotor. Thus, it is desirable to utilize a testing technique that is adaptable for flaw detection from the bore of the rotor. Although any type of radiation that may be successfully utilized with pulse-echo techniques may be employed, the use of ultrasonic waves seems most desirable.

A non-destructive ultrasonic testing approach utilized for determining flaws in a rotor by testing the bore of the rotor is described by W. R. Marklein and R. E. Warnow in a paper presented to the American Society of Mechanical Engineers at its meeting in New York Nov. 29 – Dec. 4, 1964. In this approach, ultrasonic waves in the longitudinal mode are utilized with a special plexiglass shoe or transducer mount. While this approach does have the advantage of flaw testing from the bore, with the attendant advantages over the external peripheral testing, the results do not give the completeness of information that is desirable for this type of rotor testing.

SUMMARY OF THE INVENTION

By means of the present invention, a much more complete testing of the bore of a rotor may be achieved. To accomplish this, applicant utilizes an improved testing apparatus that employs pulse-echo techniques. Ultrasonic signals or waves are utilized for this particular pulse-echo technique, although any type of appropriate radiation could be utilized. An appropriate test unit is located in the cavity of the material to be tested, such as the bore of a rotor, and is fixably stationed at the desired position by adjustable supports, such as three-legged spider arrangements. A movable carriage is mounted for reciprocable movement along the test unit and is actuated by an appropriate drive arrangement, such as an electrical motor. The precise position of the movable carriage along the test unit, and hence along the selected portion of the axis of the rotor, is determined and indicated by an appropriate indexing system.

A source conveying device, such as a plexiglass shoe, is mounted on the movable carriage for movement therewith. A source of ultrasonic waves, such as a transducer, is mounted on the source conveying means. By appropriate shaping of the plexiglass shoe, the transducer can provide ultrasonic waves in the desire mode longitudinal, shear or surface). More than one transducer may be located in a single shoe, and more than one show may be located on the movable carriage. The plexiglass shoes are maintained in contact with the walls of the cavity or bore by an appropriate bias arrangement, such as a spring or phenumatic loading. A couplant introducing system, such as a hose, is utilized to insert an appropriate liquid couplant, such as water, between the plexiglass shoes and the walls of the bore. The couplant serves to minimize the interface reflection that occurs when the ultrasonic waves pass from the plexiglass shoe into the material of the rotor and to minimize energy loss resulting from transmittal of the waves through air.

While any appropriate pulse-echo radiation may be utilized, an important aspect of this invention is to increase the amount of information produced as a result of the non-destructive testing. This is achieved by utilizing more than one mode of ultrasonic waves. In the most preferred type of testing, it is desirable to utilize all three modes of ultrasonic waves, i.e. the longitudinal, shear and surface waves. These can be utilized either simultaneously or in successive test steps. Preferably, two of the modes are used simultaneously, such as the longitudinal mode with the shear mode, and the longitudinal mode with the surface mode.

The entire test unit between the adjustable supports is rotated by an appropriate drive arrangement such as another motor. Again, appropriate indexing is utilized to precisely determine the location of the movable carriage, and hence the plexiglass shoe, in the circumferential or rotational direction. The position of the test unit along the axial direction of the bore may be varied by utilizing precision length shaft sections consecutively introduced.

In operation, the movable carriage is driven to provide both longitudinal and rotational sweeps, with the indexing apparatuses precisely locating the testing apparatus, and hence any flaws that are detected. If any flaws are present, the pulse-echo technique results in a reflected signal being detected by a pick-up device associated with the source on the plexiglass shoe to produce an output indicative of the presence of such a flaw. By utilizing this apparatus and the various modes of ultrasonic waves, the precise position of any flaw, the nature of the flaw and an accurate outline of the flaw can be achieved. In addition, the results are accurately reproducible, and hence the apparatus may be utilized at various times to determine if any flaws previously detected are showing signs of advancing or expanding.

These and other objects, advantages and features of this invention will hereinafter appear, and for purposes of illustration, but not of limitation, an exemplary embodiment of the subject invention is shown in the appended drawing.

BRIEF DESCRIPTION OF THE DRAWING

The sole figure of the drawing is a schematic perspective view of a preferred embodiment of the nondestructive test apparatus of the present invention.

DETAILED DESCRIPTION OF THE PREFERRED EMBODIMENT

With reference to the drawing, the preferred embodiment of the test apparatus is shown in detail. A test unit 1 is arranged for insertion into a cavity in the material being tested, such as a bore in a forged turbine rotor.

Test unit 1 is mounted for reciprocable motion between a pair of adjustable supports 3 and 5. Each of the supports 3 and 5 is in the form of a three-legged spider having a body portion 6 and legs 7, 9 and 11. Two of the legs, such as 7 and 9, may be mechanically or manually adjusted to fit the desired bore opening and then fixed at those positions. The third leg 11 is arranged to be biased against the wall of the bore when test unit 1 is located in the bore. The biasing arrangement for leg 11 may be any suitable type of arrangement, such as a bias spring or pneumatic loading. In the preferred embodiment disclosed herein, pneumatic loading of the leg 11 is achieved through the air lines 13 and 15. Of course, if the bore has only one opening (i.e. it is close ended), the pneumatic pressure line 15 may be derived from the pneumatic line 13.

A threaded shaft 17 extends between the adjustable supports or spiders 3 and 5. A drive shaft 19 is supported for rotation in spider 5, such as by a journal bearing. Drive shaft 19 is utilized to rotate the entire test unit 1 about the axis defined by threaded shaft 17. In addition to the threaded shaft 17, a pair of cylindrical guides or channels 21 and 23 extend between a block 25 (at spider 3) and an instrument supporting block 27 (at spider 5). Guides or channels 21 and 23 are the basic mounting supports of test unit 1 and are fixedly connected to block 25 and the instrument supporting block 27 to maintain the solidarity of test unit 1. Threaded shaft 17 is mounted for free rotation at 29 in block 25 and is driven by an appropriate drive arrangement at point 31 in instrument support block 27.

A movable carriage 33 is also mounted on the guides 21 and 23. The guides serve to support and guide the movable carriage 33 as it reciprocates between spiders 3 and 5. Threaded shaft 17 passes through the movable carriage 33 at point 35, where a threaded engagement is achieved. Mating of the threads on shaft 17 with threads in movable carriage 33 causes test unit 1 to reciprocate between spiders 3 and 5 upon rotation of shaft 17 as it is driven by the drive arrangement at 31.

A source conveying means 37 is mounted on movable carriage 33 by a pair of arms 39 and 41. Source conveying means 37 is a "shoe" that is shaped to conform to the curvature of the bore of the turbine being tested and, in the case of ultrasonic testing, is formed of a material that transmits the ultrasonic waves with a minimal loss of energy. In this preferred embodiment, a plexiglass show is utilized, although any appropriate material such as lead, some types of plastic, etc. could be used.

The plexiglass shoe 37 is maintained against the wall of the turbine with an appropriate pressure by a suitable biasing arrangement. This biasing arrangement can be of any appropriate type, such as a bias spring, but in this preferred embodiment a pneumatic pressure force is utilized. The pneumatic pressure force is applied by a pneumatic device schematically illustrated at 43.

A source of the pulse-echo rays that are to be utilized is schematically illustrated at 45. As previously indicated, the source may produce any appropriate type of radiation, but in this particular embodiment ultrasonic signals or waves are utilized. Thus, the source 45 is a transducer that produces ultrasonic waves at the desired frequency. The source 45 also incorporates a pick-up device that detects any reflected signals from flaws in the material being tested.

The ultrasonic waves produced by source 45, which are inherently in the longitudinal mode, may be modified to produce ultrasonic waves in the shear mode or the surface mode. As longitudinal mode ultrasonic waves are twisted or bent from the perpendicular to the face of the transducer of source 45, ultrasonic shear mode waves will begin to be evidenced at an angle of about 30°. Continued bending of the angle of the longitudinal waves will result in nearly complete transformation to shear waves at about 45°. Continued alteration of the angle of the ultrasonic waves will then begin to produce surface mode waves in the vicinity of 60°. Beyond about 64°, the ultrasonic waves will be almost entirely in the surface mode.

It should be noted that the shear mode waves can be directed both down the axis in the longitudinal direction and about the circumference of the bore. Similarly, the surface waves may be directed down the axis of the bore or about the circumference of the bore. For complete testing, both modes should be used in all of these fashions. As a matter of fact, the surface mode waves may also be utilized in a spiral fashion to give even better resolution.

It is not necessary that each of these tests be done in seriatim fashion, but rather, testing with more than one mode may be accomplished simultaneoulsy. Thus, a second source 47 may be located in shoe 37. Also, it is not necessary to limit the apparatus to a single shoe 37. In one form of the preferred embodiment, a second shoe (not shown) is mounted on the movable carriage 33 and extended backward toward the input end of the bore at the same angle that the legs 39 and 41 support shoe 37 in the forward direction down the bore. In addition, in the preferred embodiment it is desired to perform two separate test sequences, one combining a shear mode and a longitudinal mode and the other combining a surface mode and a longitudinal mode. In the form of the preferred embodiment referred to above in which a second shoe is utilized, a shear mode and a longitudinal mode source would be located in one shoe, while a sheer mode source would be located on the other shoe by itself. Of course, it would probably be possible to combine at three modes of operation for a simultaneous test procedure, although care would have to be exercised to avoid interference between the various modes.

The movable carriage 33 is reciprocably driven by a motor 49 which drives the threaded shaft 17 at point 31. As threaded shaft 17 is driven by motor 49, it engages the threads at 35 on movable carriage 33 and causes it to move along the guide rails 21 and 23. As the motor drives the carriage 33, an indexing arrangement 51 determines and indicates the axial position of the carriage 33. As there are various electrical and other lines, schematically indicated by the lines 53 and 55, leading to the movable carriage 33, a reel 57 is provided to receive and feed out the appropriate lines during reciprocation of carriage 33.

One of the lines 53 or 55 leading to the plexiglass head 37 is a couplant introducing device that carries a medium that serves as a couplant between the plexiglass head and the wall of the bore. This medium serves to transmit the ultrasonic waves, thus reducing energy loss in air and minimizing interface reflections.

Drive shaft 19 is actuated by a motor 59, which may be any appropriate type of driving mechanism. In this particular case, motor 59 drives a gear wheel 61 which engages a larger gear wheel 63, which is integrally connected to the drive shaft 19. An indexing device 65 is driven through a gear 67 that is in engagement with 63. In this fashion, the indexing device 65 can determine and indicate the rotational position of the plexiglass head 37.

In operation, a shield 69 on which gear wheel 63 is mounted would be secured to an appropriate support, such as by bolts 71, 73 and 75. In order to permit passage of the various electrical lines 77, pneumatic air pressure line 13 and couplant introducing line 79 (schematically illustrated), an opening 81 is provided in the shield 69.

After shield 69 has been secured in place, the test unit 1 is inserted into the bore of the turbine rotor and pneumatic pressure is applied to legs 11 of spiders 3 and 5 to secure the test unit in place. The length of the drive shaft 19 between the shield and spider 5 is accurately measured, so that the precise location of the test unit and the movable carriage 33 is known to a high degree of accuracy. The length between shield 69 and spider 5 may be adjusted by inserting additional drive shaft lengths, such as 83 and 85, which are precisely formed to a given length. In this fashion, the test unit 1 may be extended down the bore of the rotor without loss of the knowledge of its precise location, which is required for the test procedures. After spiders 3 and 5 have been secured in place, motors 57 and 59 may be actuated in any desired manner. For instance, motor 59 could be actuated to rotate the plexiglass shoe 37 a small increment in the radial direction, and then motor 49 would be actuated to provide a longitudinal sweep of the plexiglass head 37. This could be continued until longitudinal sweeps have been taken around the complete circumference of the bore.

Another approach would be to actuate motor 49 for small incremental steps of the longitudinal direction, while rotary sweeps were performed by actuation of motor 59. In practice, both types of operation would probably be utilized.

If the propagated waves contact a flaw, there is a reflection to the pick-up means at the appropriate source 45 or 47, and an appropriate indication is sent back to a recording or display device 87. By utilizing various propagation modes of the ultrasonic waves, the flaws detected may be accurately characterized and mapped. Also, as a result of the very precise and fixed locationing of the test unit 1, the test results are repeatable to a very high degree.

It should be understood that various modifications, changes and variations may be made in the arrangements, operations and detail of construction of the elements disclosed herein without departing from the spirit and scope of this invention.

I claim:

1. A non-destructive test apparatus for detecting and providing three-dimensional analysis of flaws in a horizontally positioned generally cylindrical rotor having a relatively large mass of material, a central bore with a diameter small in comparison to the diameter of the rotor and providing a test cavity being located in the rotor, comprising:

signal transmitting means to be inserted into the bore of the rotor, said signal transmitting means including at least two signal sources capable of simultaneously transmitting at least two ultrasonic signals from the bore into the mass of the rotor, said ultrasonic signals being selectively chosen from among the various ultrasonic modes;

pickup means to detect said ultrasonic signals as they are reflected from discontinuities throughout the mass of the rotor material, each of said reflected ultrasonic signals being identified with the corresponding transmitted ultrasonic signal and providing information regarding the discontinuities from which they are reflected;

position determining means providing for the direct correlation of the information content of a transmitted or reflected ultrasonic signal in one mode with the information content of reflected ultrasonic signals and unreflected transmitted ultrasonic signals in another mode, the information content of said transmitted and said reflected signals relating to discontinuity characteristics throughout the mass of the rotor material, by precisely locating in a three-dimensional matrix the path through the rotor mass of each transmitted ultrasonic signal and the position of discontinuities in the rotor material evidenced by each reflected ultrasonic signal; and recording means for preserving the information content of said transmitted and said reflected ultrasonic signals in a fashion that permits combining the individual information content of each of said transmitted and said reflected ultrasonic signals in the different modes to derive an accurate indication of the existence, position, nature size and shape of flaws in the rotor material.

2. A non-destructive test apparatus as claimed in claim 1 wherein said signal sources simultaneously transmit ultrasonic signals in different modes.

3. A non-destructive test apparatus for detecting and providing three-dimensional analysis of flaws in a horizontally positioned generally cylindrical rotor having a relatively large mass of material, a central bore with a diameter small in comparison to the diameter of the rotor and providing a test cavity being located in the rotor, comprising:

a movable carriage to be inserted into the bore of the rotor;

drive means to longitudinally advance and to rotate said movable carriage, said longitudinal advancement and said rotation being performed independently and sequentially to insure easy and accurate knowledge of the position of said movable carriage in both the longitudinal and rotational directions at all times;

a first source of ultrasonic signals to be utilized in a first mode to transmit ultrasonic signals from the bore into the mass of the rotor;

a second source of ultrasonic signals to be utilized in a second mode to transmit ultrasonic signals from the bore into the mass of the rotor simultaneously with the ultrasonic signals from said first source;

source conveying means located on said movable carriage and having said sources mounted therein, said source conveying means providing a transmitting path for ultrasonic signals from said sources;

bias means to maintain said source conveying means in engagement with the walls of the cavity;

pickup means located on said source conveying means to detect ultrasonic signals reflected from discontinuities throughout the mass of the rotor material, such reflected signals conveying information regarding the existence and nature of flaws in the rotor material;

couplant introducing means to maintain liquid couplant between said source conveying means and the walls of the cavity in the material being tested;

indexing means providing for the direct correlation of the information content of a transmitted or reflected ultrasonic signal in one mode with the information content of reflected ultrasonic signals and unreflected transmitted ultrasonic signals in another mode, the information content of said transmitted and said reflected signals relating to discontinuity characteristics throughout the mass of the rotor material, by accurately determining and indicating the axial and rotational position of said first and second sources and thus, from a knowledge of the source geometry and the characteristics of said source conveying means and the rotor material, precisely locating in a three-dimensional matrix the path through the rotor mass of each transmitted ultrasonic signal and the position of discontinuities in the rotor material evidenced by each reflected ultrasonic signal; and recording means for preserving the information content of said transmitted and said reflected ultrasonic signals in a fashion that permits combining the individual information content of each of said transmitted and said reflected ultrasonic signals in the different modes to derive an accurate indication of the existence, position, nature, size and shape of flaws in the rotor material.

4. A non-destructive test apparatus for detecting and providing three-dimensional analysis of flaws in a horizontally positioned generally cylindrical rotor having a relatively large mass of material, a central bore with a diameter small in comparison to the diameter of the rotor and providing a test cavity being located in the rotor, comprising:

a test unit to be inserted into the bore of the rotor;

adjustable support means to fixedly mount said test unit at a predetermined location in the bore of the rotor;

a movable carriage mounted for reciprocal movement along said test unit;

first drive means mounted on said test unit to drive said movable carriage along said test unit;

first indexing means to accurately determine and indicate the position of said movable carriage along said test unit;

a first source of ultrasonic signals to transmit ultrasonic signals from the bore into the mass of the rotor;

a second source of ultrasonic signals to transmit ultrasonic signals from the bore into the mass of the rotor simultaneously with the ultrasonic signals from said first source, the ultrasonic signals of said sources being selectively chosen from the various modes;

source conveying means located on said movable carriage and having said sources mounted therein, said source conveying means providing an ultrasonic signal transmitting path to the wall of the bore;

pickup means on said source conveying means to detect ultrasonic signals reflected from discontinuities throughout the mass of the rotor material, said reflected signals conveying information regarding the existence and nature of the discontinuities in the rotor material;

bias means to urge said source conveying means toward the walls of the bore in the rotor being tested;

couplant introducing means to maintain liquid couplant between said source conveying means and the walls of the bore in the rotor being tested;

second drive means outside of the bore to rotate said test unit as a unitary structure;

second indexing means to accurately determine and indicate the position of said test unit in the circumferential direction, said first and second indexing means providing for the direct correlation of the information content of a transmitted or reflected ultrasonic signal in one mode with the information content of reflected ultrasonic signals and unreflected transmitted ultrasonic signals in another mode, the information content of said transmitted and said reflected signals relating to discontinuity characteristics throughout the mass of the rotor material, by accurately determining and indicating the axial and rotational position of said first and second sources and thus, from a knowledge of the source geometry and the characteristics of said source conveying means and the rotor material, precisely locating in a three-dimensional matrix the path through the rotor mass of each transmitted ultrasonic signal and the position of discontinuities in the rotor material evidenced by each reflected ultrasonic signal; and recording means for preserving the information content of said transmitted and said reflected ultrasonic signals in a fashion that permits combining the individual information content of each of said transmitted and said reflected ultrasonic signals in the different modes to derive an accurate indication of the existence, position, nature, size and shape of flaws in the rotor material.

5. A non-destructive apparatus as claimed in claim 4 wherein:

said adjustable support means comprises first and second spiders each having first, second and third legs, said first and second legs being fixedly adjustable and said third leg being pneumatically adjustable;

said test unit further comprises guides extending between said adjustable support means to mount said movable carriage for movement therealong, and a threaded shaft to engage threads on said movable carriage and actuated by said first drive means, rotation of said shaft by said first drive means producing movement of said movable carriage along said guides; and said bias means comprises a pneumatic pressure to cause said source conveying means to engage the walls of the bore with a constant pressure.

6. A non-destructive test apparatus for detecting and providing three-dimensional analysis of flaws in a horizontally positioned generally cylindrical rotor having a relatively large mass of material, a central bore with a diameter small in comparison to the diameter of the rotor and providing a test cavity being located in the rotor, comprising:

a test unit to be inserted into the bore a precisely determined distance;

a support structure at each end of said test unit to mount said test unit, each of said support structures being adjustable to snugly fit various size bores and remain stationary except when being moved along the bore;

a pair of guide rails extending between said support structures;

a movable carriage mounted on said guide rails for axial advancement along said test unit, said movable carriage having a threaded opening therein;

a threaded rod extending through said threaded opening, the threads on said threaded rod engaging the threads of said threaded opening;

a first drive motor mounted on said test unit and rotationally driving said threaded rod, rotation of said threaded rod producing axial movement of said movable carriage along said guide rails;

first indexing means to accurately determine and indicate the position of said movable carriage along said test unit;

a solid ultrasonic transmitting shoe mounted on said movable carriage;

a first source of ultrasonic signals to produce ultrasonic signals to be utilized in a first mode for scanning the surface of the bore, said first source being mounted in said shoe;

a second source of ultrasonic signals to produce ultrasonic signals to be utilized in a second mode for scanning the surface of the bore, said second source being mounted in said shoe;

bias means to urge said shoe against the surface of the bore with a constant force;

couplant introducing means to maintain a liquid couplant between said shoe and the surface of the bore;

a second drive motor positioned outside of the bore to rotate the test unit;

pickup means on said shoe to detect ultrasonic signals from said first and second sources that are reflected from discontinuities throughout the mass of the materials of the rotor, such reflected signals conveying information regarding the existence and nature of flaws in the rotor;

second indexing means to accurately determine and indicate the position of said test unit in the circumferential direction, said first and second indexing means providing for the direct correlation of the information content of a transmitted or reflected ultrasonic signal in one mode with the information content of reflected ultrasonic signals and unreflected transmitted ultrasonic signals in other modes, the information content of said transmitted and said reflected signals relating to discontinuity characteristics throughout the mass of the rotor material, by accurately determining and indicating the axial and rotational position of said first and second sources and thus, from a knowledge of the source geometry and the characteristics of said source conveying means and the rotor material, precisely locating in a three-dimensional matrix the path through the rotor mass of each transmitted ultrasonic signal and the position of discontinuities in the rotor material evidenced by each reflected ultrasonic signal; and recording means for preserving the information content of said transmitted and said reflected ultrasonic signals in a fashion that permits combining the individual information content of each of said transmitted and said reflected ultrasonic signals in the different modes to derive an accurate indication of the existence, position, nature, size and shape of flaws in the rotor material.

7. A method for detecting and providing three-dimensional analysis of flaws in a horizontally positioned generally cylindrical rotor having a relatively large mass of material, a central bore having a diameter small in comparison to the diameter of the rotor and providing a test cavity being located in th rotor, comprising the steps:

transmitting more than one mode of ultrasonic signals from the bore into the mass of the rotor;

detecting signals reflected from discontinuities in the rotor material for each mode of ultrasonic signals utilized, said reflected signals conveying information regarding the existence and nature of discontinuities throughout the mass of the rotor material;

identifying each of said reflected ultrasonic signals with the corresponding transmitted ultrasonic signal;

correlating the information content of a transmitted or reflected ultrasonic signal in one mode with the information content of reflected ultrasonic signals and unreflected transmitted ultrasonic signals in another mode, the information content of said transmitted and said reflected signals relating to discontinuity characteristics throughout the mass of the rotor material, by accurately determining in a three-dimensional matrix the path through the rotor mass of each transmitted ultrasonic signal and the location of discontinuities in the rotor material evidenced by each reflected ultrasonic signal; and combining the information content of said transmitted and said reflected ultrasonic signals in the different modes to derive an accurate indication of the position, nature, size and shape of flaws in the rotor material.

8. A method for detecting and providing three-dimensional analysis of flaws in a horizontally positioned generally cylindrical rotor having a relatively large mass of material, a central bore having a diameter small in comparison to the diameter of the rotor and providing a test cavity being located in the rotor, comprising the steps:

transmitting a first mode of ultrasonic signals produced by a first source of ultrasonic signals from the bore into the mass of the rotor;

accurately determining the position of said first source at all times during the transmission of ultrasonic signals therefrom into the mass of the rotor;

detecting ultrasonic signals from said first source that are reflected from discontinuities in the rotor material, said reflected signals conveying information regarding the existence and nature of flaws in the rotor material;

recording the information conveyed by reflected ultrasonic signals originally transmitted from said first source as a function of the position of said first source;

transmitting a second mode of ultrasonic signals produced by a second source of ultrasonic signals from the bore into the mass of the rotor;

accurately determining the position of said second source at all times during the transmission of ultrasonic signals therefrom into the mass of the rotor;

detecting ultrasonic signals from second source that are reflected from discontinuities in the rotor material, said reflected signals conveying information regarding the existence and nature of flaws in the rotor material, the discontinuities from which the ultrasonic signals of said first and second sources are reflected being located throughout the mass of the rotor material;

recording the information conveyed by reflected ultrasonic signals originally transmitted from said second source as a function of the position of said second source;

correlating the information content of a transmitted or reflected ultrasonic signal in one mode with the information content of reflected ultrasonic signals and unreflected transmitted ultrasonic signals in another mode, the information content of said transmitted and said reflected signals relating to discontinuity characteristics throughout the mass of the rotor material, by accurately determining in a three-dimensional matrix the path through the rotor mass of each transmitted ultrasonic signal and the location of discontinuities in the rotor material evidenced by each reflected ultrasonic signal; and combining the information content of said transmitted and said reflected ultrasonic signals in the different modes to derive an accurate indication of the position, nature, size and shape of flaws in the rotor material.

9. A method as claimed in claim 8 and further comprising the steps:

transmitting a third mode of ultrasonic signals produced by a third source of ultrasonic signals from the bore into the mass of the rotor;

accurately determining the position of said third source at all times during the transmission of ultrasonic signals therefrom into the mass of the rotor;

detecting ultrasonic signals from said third source that are reflected from discontinuities in the rotor material, said reflected signals conveying information regarding the existence and nature of flaws in the rotor material; and recording the information conveyed by reflected ultrasonic signals originally transmitted from said third source as a function of the position of said third source.

10. A method as claimed in claim 8 and further comprising the step of repeating the steps of claim 8 at a subsequent time to determine if flaw removal has been successful or if flaw characteristics have changed with the passage of time.

11. A method for detecting and providing three-dimensional analysis of flaws in a horizontally positioned generally cylindrical rotor having a relatively large mass of material, a central bore having a diameter small in comparison to the diameter of the rotor and providing aa test cavity being located in the rotor, comprising the steps:

repetitively indexing a first source of ultrasonic signals, said first source being adapted for motion in both the axial and circumferential directions, to move in incremental steps in one of said directions, said first source producing ultrasonic signals to be utilized in a first mode;

acuating said first source to have said first mode ultrasonic signals scan the bore in the other of said directions of motion after each of said incremental steps;

accurately determining the position of said first source in both the axial and circumferential directions at all times;

detecting by pulse-echo techniques ultrasonic signals from said first source that are reflected from discontinuities in material of the rotor, such reflected signals conveying information regarding the existence and nature of flaws in the rotor;

recording the information conveyed by the reflected ultrasonic signals from said first source as a function of the axial and circumferential position of said first source.

repetitively indexing a second source of ultrasonic signals, said second source being adapted for motion in both the axial and circumferential directions, to move in incremental steps in one of said directions, said second source producing ultrasonic signals to be utilized in a second mode;

actuating said second source to have said second mode ultrasonic signals scan the bore in the other of said directions of motion after each of said incremental steps;

accurately determining the position of said second source in both the axial and circumferential directions at all times;

detecting by pulse-echo techniques ultrasonic signals from said second source that are reflected from discontinuities in the material of the rotor, such reflected signals conveying information regarding the existence and nature of flaws in the rotor;

recording the information conveyed by the reflected ultrasonic signals from said second source as a function of the axial and circumferential position of said second source;

repetitively indexing third source of ultrasonic signals, said third source being adapted for motion in both the axial and circumferential directions, to move in incremental steps in one of said directions, said third source producing ultrasonic signals to be utilized in a third mode;

actuating said third source to have said third mode ultrasonic signals scan the bore in the other of said directions of motion after each of said incremental steps;

detecting by pulse-echo techniques ultrasonic signals from said third source that are reflected from discontinuities in the material of the rotor, such reflected signals conveying inormation regarding the existence and nature of flaws in the rotor, the discontinuities from which the ultrasonic signals of said first, second and third sources are reflected being located throughout the mass of the rotor material;

recording the information conveyed by the reflected ultrasonic signals from said third source as a function of the axial and circumferential position of said third source;

correlating the information content of a transmitted or reflected ultrasonic signal in one mode with the information content of reflected ultrasonic signals and unreflected transmitted ultrasonic signals in other modes by accurately determining in a three-dimensional matrix the path through the rotor mass of each transmitted ultrasonic signal and the location of discontinuities in the rotor material evidenced by each reflected ultrasonic signal; and combining the information content of said transmitted and said reflected ultrasonic signals in the different modes to derive an accurate indication of the position, nature, size and shape of flaws in the rotor material.

12. A method as claimed in claim 11 wherein said sources are indexed in the axial direction and scanned in the circumferential direction.

13. A method as claimed in claim 11 wherein said sources re indexed in the circumferential direction and scanned in the axial direction.

* * * * *

UNITED STATES PATENT AND TRADEMARK OFFICE
CERTIFICATE OF CORRECTION

PATENT NO. : 3,960,006
DATED : June 1, 1976
INVENTOR(S) : Robert D. Smith

It is certified that error appears in the above-identified patent and that said Letters Patent are hereby corrected as shown below:

Column 2, line 26, delete the word "desire" and insert therefor --desired--;

line 27, before the word "longitudinal" insert a parenthesis [(];

line 29, delete the word "show" and insert therefor --shoe--;

Column 4, line 6, delete the word "show" and insert therefor --shoe--;

line 66, delete the word "sheer" and insert therefor --shear--;

line 68, delete the word "at" and insert therefor --all--;

Column 5, line 61, delete the word "of" and insert therefor --in--;

Column 6, line 53, after the word "nature" insert a comma [,];

Column 10, line 30, delete the word "th" and insert therefor --the--;

Column 12, line 9, delete the word "aa" and insert therefor --a--;

line 55, before the word "indexing" insert --a--; and

Column 14, line 14, delete the word "re" and insert therefor --are--.

Signed and Sealed this

Eleventh Day of January 1977

[SEAL]

Attest:

RUTH C. MASON
*Attesting Officer*

C. MARSHALL DANN
*Commissioner of Patents and Trademarks*